United States Patent [19]

Oron et al.

[11] Patent Number: 5,080,671
[45] Date of Patent: Jan. 14, 1992

[54] METHOD OF TREATING A METAL PROSTHETIC DEVICE PRIOR TO SURGICAL IMPLANTATION TO ENHANCE BONE GROWTH RELATIVE THERETO FOLLOWING IMPLANTATION

[76] Inventors: Uri Oron, 3 Horovitz Street, Rishon Lezion 75233; Roni Hazan, 29 Gush-Ezion Street, Tel-Aviv, both of Israel

[21] Appl. No.: 387,439

[22] Filed: Jul. 31, 1989

Related U.S. Application Data

[63] Continuation of Ser. No. 125,145, Nov. 25, 1987, abandoned, which is a continuation-in-part of Ser. No. 885,159, Jul. 14, 1986, abandoned.

[51] Int. Cl.⁵ .............................. A61F 2/28; A61F 2/54
[52] U.S. Cl. ............................................ 623/16; 623/66; 623/901; 427/2; 433/201.1
[58] Field of Search ........ 128/92 YQ, 92 YG, 92 YE; 148/12 E, 135; 427/2; 433/201.1, 229; 623/11, 16, 16 A, 16 F, 66, 901

[56] References Cited

U.S. PATENT DOCUMENTS

| | | | |
|---|---|---|---|
| 3,097,980 | 7/1963 | Swarr et al. | 148/135 |
| 3,605,123 | 9/1971 | Hahn | 3/1 |
| 3,643,658 | 2/1972 | Steinemenan | 128/92 |
| 3,855,638 | 12/1974 | Pilliar | 3/1 |
| 3,905,777 | 9/1975 | Lacroix | 29/183.5 |
| 3,919,723 | 11/1975 | Heimke et al. | 3/1.9 |
| 3,964,473 | 6/1976 | Wickham et al. | 128/82.1 |
| 4,040,129 | 8/1977 | Steinemann | 3/1.9 |
| 4,234,972 | 11/1980 | Hench et al. | 3/1.9 |
| 4,365,356 | 12/1982 | Broemer et al. | 3/1.9 |
| 4,427,501 | 1/1984 | Rogers | 204/37 |
| 4,466,991 | 8/1984 | Andreev et al. | 427/38 |
| 4,476,590 | 10/1984 | Scales et al. | 3/1.91 |
| 4,536,894 | 8/1985 | Galante et al. | 623/22 |
| 4,718,908 | 1/1988 | Wigginton et al. | 623/16 |
| 4,775,426 | 10/1988 | Murley et al. | 623/16 |

*Primary Examiner*—Randall L. Green
*Assistant Examiner*—Paul Prebilic
*Attorney, Agent, or Firm*—Body, Vickers & Daniels

[57] ABSTRACT

Metal prosthetic devices to be surgically implanted are heated prior to implantation thereof to a temperature between 110° C. and 430° C. for a period of from twenty minutes to three hours. Such heating enhances bone growth relative to the prosthetic device following implantation.

11 Claims, No Drawings

METHOD OF TREATING A METAL PROSTHETIC DEVICE PRIOR TO SURGICAL IMPLANTATION TO ENHANCE BONE GROWTH RELATIVE THERETO FOLLOWING IMPLANTATION

This is a continuation-in-part of Ser. No. 125,145 filed Nov. 25, 1987 now abandoned, which in turn is a continuation-in-part of Ser. No. 885,159, filed July 14, 1986, now abandoned.

BACKGROUND OF THE INVENTION

This invention relates to the art of prosthetic devices and, more particularly, to the treatment of metal or metal portions of prosthetic devices, and devices resulting from such treatment.

It is of course well known that metal prosthetic devices or such devices including exposed metallic surfaces have been provided for applications including, for example, orthopedic surgery and dentistry in human and or veterinary medicine. Such prosthetic devices include, for example, artificial joints, artificial teeth, special reconstructive surgery devices including plates and screws, and the like. The devices, or the metallic portions thereof, are constructed of metals or metal alloys which are not corroded or otherwise degraded by body fluids. A fundamental obstacle to the long term success or metal prosthetic implants is the permanent fixation of the prosthetic device to the bone in which it is received. Heretofore, it has not been possible to achieve a good bond directly between bone and metal, whereby considerable effort has been made to develop special bonding techniques.

At the present time, prosthetic implants are secured in place in the bone primarily through the use of cements and adhesives. Hip and knee joint replacements are common surgical procedures today in which such adhesive bonding is used, and studies have shown loosening or migration of the implant in up to fifty percent of the cemented femoral components of total hip replacement and in conventional acetabular components of the hip joint. Loss of fixation is particularly prevalent in young adults with up to fifty-seven percent demonstrating radiolucent lines around the metal implant and/or migration of the components and/or the need for corrective surgery within five years of the implantation. The interface between the bone and cement is generally the point of failure. Such failure is due to mechanical forces that weaken the bond between the bone and cement, and to deterioration of the cement as the result of time and other factors. Although methods have been developed to improve the bone cement and its application, the inherent limitations of bone cement are increasingly apparent in that the long term failure rates remain unacceptably high. Furthermore, there have been reports of adverse effects of the cement on the recipient of the implant including toxic reaction and sciatic nerve entrapment.

It has been suggested that the natural ingrowth of bone into porous metal surfaces of prosthetic implants might provide a clinically acceptable alternative to the use of cements and adhesives. In this respect, it is believed that bone ingrowth to irregular surfaces of an implant would produce a good bond therebetween. Such natural ingrowth of bone has been found to provide an interfacial strength between the bone and implant which is sufficient to support load bearing prosthesis. However, in order to provide long term stabilization, sufficient bone ingrowth must occur in the initial phase after implantation. In order to achieve sufficient bone ingrowth in this respect, at the present time the prosthesis has to be fixed in a stable position without movement for a period of at least six weeks in humans, and any relative motion of the prosthesis during this period either prevents or minimizes bone growth and can lead to formation of scar tissue instead of bone ingrowth. Clinical data shows that even under optimal conditions, some areas of the implant may display no bone growth.

Efforts to overcome the foregoing problems have included, for example, providing the exposed metallic portions of prosthetic devices with porous coatings, such as disclosed in U.S. Pat. No. 3,855,638 to Pilliar, providing the prosthetic device with wedge-shaped bone ingrowth materials, as shown in U.S. Pat. No. 4,536,894 to Glalante et al, and providing the prosthetic device with electrodes to influence bone growth by means of stimulating electric potential. These approaches have not overcome the problems of long term failure and long term immobilization. Other efforts, likewise unsuccessful in overcoming the foregoing problems, have included the coating of the prosthetic device with a bio-active material such as enamel or glass or glass-ceramic material, as respectively shown in U.S. Pat. Nos. 4,365,536 to Broemer et al and 4,234,972 to Hench et al. None of the previous efforts has resulted in increasing the interfacial shear strength between an implant and bone so as to significantly improve on the problem of long term failure. Further, the efforts to achieve bone ingrowth into implants have not provided sufficient bone growth to avoid the minimum six week period of immobilization following implantation in order to enhance long term stabilization.

It will be appreciated that enhancement of stabilization of implants is not only beneficial in joint replacement as discussed above but also in all dental implants, and implants designed to bridge a gap between bone ends caused by removal of a portion of the bone. The latter can be of particular importance in connection with certain humans, such as the elderly and chronic rheumatic disease patients, or other persons that have a limited or lesser than normal potential for bone regeneration.

DETAILED DESCRIPTION OF THE INVENTION

In accordance with the present invention, the foregoing problems regarding shear strength and long term failure, and the requirement for long term immobilization immediately following the implantation of the prosthetic device are advantageously minimized or overcome. More particularly in this respect, a metal or metal portion of a prosthetic implant is heat treated prior to implantation, and such heat treating promotes both the degree of bone growth inwardly relative to the implant and the rate of such bone growth. Following a given period of implantation, the shear strength at the interface between the bone and prosthetic device heat treated in accordance with the present invention is increased up to three to four times that achieved with the same prosthetic device when implanted in accordance with present procedures wherein the device is sterilized in a steam autoclave to a temperature of about 120° C. to 140° C. and then implanted. Moreover, a prosthetic implant heat treated in accordance with the invention is ready for implantation immediately following the heat treating procedure, or can be stored for later use in that it remains effective to promote the degree and rate of bone growth upon implantation after a considerable period of time following the heat treating process.

More particularly in accordance with the present invention, metal prosthetic devices are heated to a temperature of from about 110° C. to about 430° C., preferably in a dry atmosphere, and preferably for a period of time of from about twenty minutes to about three hours. The heat treating procedure is simple, inexpensive and does not require either qualified professional personnel or the use of sophisticated equipment. Further in accordance with the invention, the time and temperature at which the heat treatment is performed can be varied, and this advantageously enables controlling the degree and rate of bone growth following implantation. This provides considerable versatility with respect to clinical applications wherein, for example, such factors as the normal rate of bone growth or regeneration vary between patients. Versatility is also provided in that a prosthetic implant device treated in accordance with the invention can be immediately implanted or can be implanted without any significant reduction in the degree and rate of bone growth for a period up to at least five weeks following heat treatment.

It is accordingly an outstanding object of the present invention to provide improvements in connection with the long term stability of metal prosthetic implant devices.

Another object is the provision of improvements in connection with reducing the immobilization time required following implanting of metal prosthetic devices.

Still another object is the provision of a method of treatment metal or metal portions of prosthetic devices to promote the degree and rate of bone growth relative thereto following implantation.

Still another object is the provision of a method of treatment metal or metal portions of prosthetic devices which enables selectively controlling the degree and rate of bone growth relative thereto following implantation.

DETAILED DESCRIPTION OF THE INVENTION

The present invention is predicated upon the discovery that the heating of a metal prosthetic device in a dry atmosphere to and above a temperature to which such devices are normally heated in connection with sterilization, which is generally about 130° C. to 140° C., enhances both the degree and rate of bone ingrowth to the prosthetic device following implantation thereof. In connection with this discovery, a number of studies or experiments were conducted on laboratory animals in an effort to determine preferred parameters with respect to temperature of heating, time of heating, the effect of delayed implantation, applicability to various metals used in making prosthetic devices, and the effect of different gaseous environments in which the devices are heat treated. Two of the studies involved comparisons with implants sterilized in a steam autoclave in accordance with present implant surgical procedures.

In connection with studies made, which are charted herein, an animal model, namely laboratory rats, was established to enable a quantitative and qualitative analysis of the tissue growth into metal implants. The animal models were mature female Wistar rats weighing between 180 to 200 grams and, in connection with the implantations, surgery was performed in which the distal condyle of the femur was removed by transverse sectioning at the level of the proximal end of the patellar groove. A small tapered dental screw was introduced into the medullary canal of the femur to create an unobstructed pathway for the subsequent insertion of the surgical screw that served as the test implant device. This procedure results in breakage of the bone trabeculae while the cortical bone remains intact. The metal implant in all of the studies with one exception which will be apparent hereinafter, was defined by a small metal surgical screw known as a cortical screw and which measures 2 millimeters in diameter by 8 millimeters in length and has a thread depth of about 0.7 millimeters. In heat treating the implants in accordance with the present invention, the latter were placed in a small covered glass petri-dish in a stainless steel incubator preheated to a selected temperature and in an environment of air, oxygen or other gas for a predetermined period of time. With respect to the gas environment, the incubator was flushed and then saturated to one atmosphere of pressure with the selected gas and after the implants were placed in the incubator. The incubator was then heated to the desired temperature and the implants heated for the desired period of time. The implants were removed from the incubator and exposed to a room temperature of about 20° C. This procedure precluded surgical preparations of the laboratory animal by about one day, with the exception of a study made to determine shelf life of the heat treated implants.

The implant screw was carefully inserted by pushing, as opposed to screwing, into the medullary canal with the head of the screw protruding from the distal end of the femur. Care was taken to ensure that the screw would fit tightly but could be pulled out with minimal force immediately following insertion thereof. In all of the studies made, the interfacial shear strength between the implant and bone was measured to provide data representative of both the degree and rate of bone growth, and the device employed to measure the shear strength was secured relative to the head of the screw and the femur of the test animal and included a steel basket into which weights were added in increments of about 200 grams each until the implanted screw was completely pulled out. The shear strength was defined as the total weight in the basket at the moment the screw was pulled out divided by the surface area of the screw in contact with the bone. The results in connection with each evaluation were statistically evaluated using single classification analysis of variance and Student Neuman-Keul test for multiple comparison among means. The value P (confidence probability) for significant difference was 0.05 or less ($P<0.05$). In each of the tables hereafter, the results are presented as means ± standard deviation.

STUDY I

An initial study was made for the purpose of comparing the degree and rate of bone growth between identical surgical screw implants of commercial stainless steel 316L having the foregoing dimensions and one of which screws was heat treated by heating in an incubator at 280° C. for three hours at one atmosphere of air, and the other of which screws were sterilized by standard procedure in an autoclave at approximately 130° C. and 1.2 atmosphere for fifty minutes. For purposes of this evaluation, six laboratory animals were used to measure the shear strength immediately after insertion of the implant, namely the zero time interval, and the shear strength at this point was found to be about 0.1 kg/cm² and thus negligible.

As will be seen from Table I below, the shear strength against removal of the implants was determined at different time periods following implantation and with respect to a number of laboratory animals for each time period and for each of the two implants.

TABLE I

| | STERILIZED IMPLANT | | HEAT TREATED IMPLANT | |
|---|---|---|---|---|
| PERIOD OF IMPLANTATION (DAYS) | ANIMALS TESTED (NUMBER) | SHEAR STRENGTH (kg/cm²) | ANIMALS TESTED (NUMBER) | SHEAR STRENGTH (kg/cm²) |
| 7 | 9 | 1.45 ± 1.24 | 6 | 6.08 ± 2.32 |
| 14 | 9 | 4.66 ± 1.86 | 7 | 9.06 ± 4.39 |
| 21 | 7 | 5.97 ± 3.46 | 10 | 11.62 ± 4.58 |

As will be seen from Table I, bone growth within the first time period was about 4.2 times greater with the heat treated implant than with the sterilized implant and remained about 2.0 times higher for each of the time periods thereafter. Both the sterilized and heat treated implants showed significant ($P<0.01$) progressive increases in the force of dislodgement of the screw from the femur with time.

Further in connection with the above study, three of the laboratory animals for each of the time intervals were used for histological evaluation of bone growth in the light microscope level. In this respect, the femur was prepared for histology by carefully unscrewing the screw and transferring it to a Bouin's fixative for seven days. The femur was then decalcified in Clark's decalcification solution (23% formic acid and 3.4% sodium format in water) at about 20° C. for three weeks. The latter solution was replaced each day. After dehydration in alcohol and embedding in parafin, sections measuring about 8-10 um were stained with Massons' Trichrome. Photographs were then taken using a Zeiss microscope. This histological examination indicated the progressive formation of bone around the screw as is indicated by the progressive increase in shear strength in Table I. At the initial stage of the histological examination, active osteoblasts were seen in the grooves between the ridges of the screws followed by the formation of woven bone. Later on, calcified trabecuale and compact bone was seen around the screw. Thus, the progressive increase in required force of dislodgement with time as shown in Table I accurately reflects growth of bone into the grooves between the threads of the screws. It should be further noted that examination of histological sections of the tissue growth around the heat treated versus the sterilized implants indicated that, qualitatively, the overall process of bone growth was similar even though it was much more enhanced around the heat treated implant. Thus, the heat treatment of the implant does not affect the regular bone growth around implants. Further, the histological sections around the tissue adjacent to the heat treated implants did not show any pathological features of provoked tissue reaction. Therefore, there is no indication of any adverse effects of the heat treatment on the bone tissue surrounding a heat treated implant.

STUDY II

In another series of experiments, the applicability of heat treating implants in accordance with the present invention as described hereinabove in connection with stainless steel 316L was determined with regard to other metals known in the metal implant art and which have been medically approved. The implants in these experiments were surgical screws produced from the metals listed in Table II below and, additionally, cylinders of titanium mesh provided in a shape currently used in hip joint replacements in humans. Again, implants sterilized in an autoclave at about 130° C. and implants heat treated in this instance by heating to 280° C. for twenty minutes in air in a stainless steel incubator were compared on the basis of the shear strength against extraction following corresponding periods of implantation. In connection with the alloys used, VITALUM is a cobalt-chromuim-molybdenum alloy and TIVANIUM is a titanium-aluminum-vanadium alloy.

TABLE II

| METAL OR ALLOY | PERIOD OF IMPLANTATION (DAYS) | STERILIZED IMPLANT | | HEAT TREATED IMPLANT | |
|---|---|---|---|---|---|
| | | ANIMALS TESTED (NUMBER) | SHEAR STRENGTH (kg/cm²) | ANIMALS TESTED (NUMBER) | SHEAR STRENGTH (kg/cm²) |
| TIVANIUM | 7 | 12 | 8.62 ± 4.70 | 8 | 12.10 ± 5.30 |
| TIVANIUM | 14 | 7 | 7.93 ± 2.15 | 7 | 15.68 ± 5.06 |
| VITALIUM | 6 | 4 | 4.80 ± 2.80 | 4 | 8.40 ± 2.84 |
| Titanium | 8 | 4 | 9.40 ± 3.00 | 8 | 15.52 ± 4.43 |
| Titanium Mesh | 6 | 8 | 2.02 ± 0.53 | 8 | 4.46 ± 2.21 |

It will be appreciated from the results in Table II that the metals and alloys heat treated in accordance with the present invention provide a shear strength from about 1.4 to about 2.2 times that provided for an implant of the corresponding material which is sterilized in a steam autoclave. Such an increase in shear strength is of course indicative of increases in both the degree and rate of bone growth.

STUDY III

Experiments were also conducted to assess the effect of various temperatures of heat treating on the shear strength of the implants. The results of these experiments are set forth below in Table III and, in connection with these experiments, the implants were surgical screws of stainless steel 316L having the dimensions identified at the outset hereof. The screws were heated in air in a stainless steel incubator for twenty minutes, implanted into laboratory animals as described at the outset hereof, and the shear strength was measured in each instance two weeks after the implantation.

TABLE III

| Temperature (°C.) | Animals Tested (number) | Shear Strength (kg/cm²) |
| --- | --- | --- |
| 110 | 5 | 6.42 ± 2.12 |
| 140 | 5 | 7.10 ± 2.80 |
| 200 | 6 | 6.72 ± 1.94 |
| 250 | 5 | 11.33 ± 2.30 |
| 280 | 6 | 16.43 ± 4.50 |
| 300 | 10 | 16.23 ± 3.58 |
| 430 | 5 | 10.80 ± 3.82 |

It will be appreciated from the data in Table III that the statistical analysis indicated a progressive and significant increase in shear strength and thus in the degree and rate of bone growth in the temperature range of from 250° C. to about 280° C. and thereafter a decrease. It is concluded, therefore, that the temperature is important for pretreatment and plays a major role in the enhancement of bone growth into the implants and, at the same time, provides a way to control the degree of bone growth for a given period of implantation. As will be further appreciated from Table III, a temperature range of from 250° C. to 430° C. produced the highest degree and rate of bone growth with the optimum temperature relative to a two week period of implantation being 280° C.

STUDY IV

Table IV sets forth the results of experiments to determine the effect of the time of heating of the implants to a fixed temperature on the shear strength of the implants in the bone. The implants in connection with these experiments were surgical screws of stainless steel 316L heated in air in a stainless steel incubator, and the shear strength was measured after a period of implantation of two weeks. The data for 280° C. and 20 minutes is taken from Study III.

TABLE IV

| Temperature (°C.) | Heating Time (minutes) | Animals Tested (number) | Shear Strength (kg/cm²) |
| --- | --- | --- | --- |
| 250 | 20 | 5 | 11.33 ± 2.30 |
| 250 | 180 | 5 | 8.22 ± 3.42 |
| 280 | 20 | 9 | 16.43 ± 4.50 |
| 280 | 60 | 5 | 10.01 ± 2.64 |
| 280 | 180 | 6 | 9.95 ± 3.91 |
| 280 | 600 | 4 | 9.80 ± 5.10 |

The results of the experiments tabulated in Table IV verify that the optimum temperature and time for preheating the stainless steel implants is 280° C. for twenty minutes in that the heating of the implants at the temperatures indicated for periods greater than twenty minutes results in a decrease in shear strength with respect to the removal of the implants after a two week period of implantation.

It will be noted at this point that the shear strength in Table IV at 280° C. for three hours is higher than that indicated in Table I for the same temperature, time period of heating and period if implantation. The reason for the difference is that the studies subsequent to Study I were done under conditions of optimum sterilization of the laboratory animals, operating environment and surgical devices, whereas the first study was done under less strict conditions. In this respect, for example, in Study I the animals were only sterilized in the area of the surgery, sterile gloves were not worn, and the operating environment was not fully sterilized.

STUDY V

In each of the foregoing experiments the metal implants were heated in an atmosphere of air. In order to determine whether the gaseous environment in which the implant is heated has an effect on the degree and rate of bone growth following implantation, surgical screw implants of stainless steel 316L were heated for twenty minutes at 280° C. in atmosphere of 100% oxygen and nitrogen, and for forty minutes in a steam autoclave at about 130° C. The screws were implanted in laboratory animals for a period of two weeks, and the shear strengths of the implantations were then measured. The results of these experiments are set forth below in Table V. The data for heating implants in air is taken from Study III.

TABLE V

| Gas Composition | Temperature (°C.) Time (Min.) | Animals Tested (number) | Shear Strength (kg/cm²) |
| --- | --- | --- | --- |
| Air | 280°/20 | 9 | 16.43 ± 4.50 |
| 100% $O_2$ | 280°/20 | 8 | 14.42 ± 3.80 |
| 100% $N_2$ | 280°/20 | 6 | 5.59 ± 1.94 |
| Autoclave | 130°/40 | 6 | 8.98 ± 2.20 |

It will be seen from the results tabulated in Table V that heating of the implants in pure oxygen provides substantially the same degree and rate of bone growth following implantation as that provided by implants heated in an atmosphere of air, whereas heating of the implants in an atmosphere of pure nitrogen results in a significant reduction in the degree and rate of bone growth. It is also noted that heating in a humid air atmosphere such as a steam autoclave results in a reduction in bone growth relative to air or oxygen, but an increase relative to nitrogen. The results indicate that the rate of bone growth can be affected dramatically by possible change in physical and chemical properties of the surface of the metal implant that is in immediate contact with the cells in the marrow cavity. In other words, the surface of the implant becomes oxidized to an extent dependent on the amount of oxygen coupled to the metals during heating. Indeed, the results show that, in an environment devoid of oxygen, heating resulted in bone growth that was even less than that indicated with sterilization in a humid atmosphere and which, in turn, is less than that indicated with dry air and oxygen.

STUDY VI

Experiments were also conducted to evaluate the shelf-life of implants heat treated in accordance with the present invention. For purposes of these experiments, the implants were surgical screws of stainless steel 316L heated at 280° C. for twenty minutes in an atmosphere of air. The implants were then divided into three groups of eight each, and the implants of one group were immediately implanted in laboratory animals in a manner described herein while the second and third groups of implants were kept at room temperature of about 20° C. to 25° C. in sterile conditions. After one week, the second group of implants was inserted into laboratory animals and, after five weeks, the third group was inserted into laboratory animals. The period of implantation for each of the groups of implants was two weeks following which the shear strength was measured as described herein.

No statistical difference was found between the shear strength in each of the three groups of implants and that recorded hereinabove for the implants heated at 280° C. for twenty minutes. Accordingly, implants heat treated in accordance with the present invention remain effective and still enhance bone growth into the implants for a considerable period of time following the heat treatment, whereby it is not necessary to achieve the heat treatment at the time of the implantation process. Thus, for example, prosthetic devices can be heat treated in accordance with the present invention as a final step in their production process and then implanted in patients at a time interval after such production. It is believed that these results are further indicative of the fact that oxidation of the surfaces of the metal implants may be what promotes the increase in the degree and rate of bone growth. In this respect, oxidation of the surfaces of the implants resulting from heating would not change materially following the treatment, whereby the oxidized surface of the implant remains effective for a considerable period after treatment.

STUDY VII

The effect of the heat treatment on the physical surface contour of the implant was investigated using a scanning electron microscope. In this respect, implants which had been heated to 280° C. for twenty minutes in an atmosphere of air were examined at a magnification of 10,000 both prior to and following the heat treatment. No change in the physical surface contour was seen in the scanning electron microscope, indicating that the optimum heat treating of implants does not cause physical structure changes in the smooth surface of the metal implants. This, of course, does not preclude the possibility of oxidation of the surfaces discussed above in that such oxidation would escape detection by electron microscopy.

The treatment of surgical prosthetic devices in accordance with the present invention provides considerable versatility and significant improvements in connection with clinical applications thereof. In this respect, in all joint replacements such as hip, knee, shoulder and elbow, wherein the prosthetic device has to be stabilized following implantation, an implanted device treated in accordance with the present invention will promote rapid initial fixation by the enhancement of bone growth thereinto thus decreasing the time that the hip, knee or other artificial joint has to remain unloaded following surgery. Thus, the recovery from such surgery may be faster, and the enhanced degree of bone growth achieved in accordance with the present invention will promote long term success of the replaced joint. Furthermore, it will be appreciated from the tabulated test results herein that it is possible to regulate the rate of bone growth relative to the implant by changing the time and/or temperature and/or gaseous environment at which the implant is heat treated. This advantageously makes it possible to construct an implant, for example, the femoral component of a hip joint, from several component parts that will eventually be put together to the final desired form. Each component part can be heat treated to provide a certain desired rate of bone growth relative thereto and according to optimum biomechanical demands for clinical considerations. Therefore, the terminology metal prosthetic device as used herein and in the appended claims is intended to be inclusive of an implant comprised of metal and/or metal alloy, and composite devices including non-metal and metal and/or metal alloy parts and/or metal alloys.

Any implant made of the alloys currently used in orthopedics and dentistry can be treated according to the present invention without the need to change the configuration or mechanical properties of such implants and which configurations and properties have been accepted for many years as being clinically successful. Such implants include, for example, those having a smooth surface, a surface defined by a porous coating, and surfaces having various degrees of roughness as a result of plasma spraying, for example. It will be understood that the terms surface and exposed surface as used herein and in the append claims is with reference to that portion of the implant designed to be secured to the bone of the recipient of the implant.

Further in connection with the above statement regarding implants made from metals and alloys currently used in orthopedics and dentistry, it is to be understood that silver is not generally acceptable today as a constituent of metal implants or as a coating for implants. More importantly, experiments using silver coated screws treated in accordance with the present invention show that such implants do not promote any measurable bone growth at all. It is known that silver becomes bioerodable when heated to or above a temperature of about 180° C., and it is believed that such erosion precludes treating a silver or silver coated implant in accordance with the invention, even if silver were acceptable. More particularly with regard to the aforementioned experiments, copper alloy screws were electrochemically coated with pure silver to provide a coating having a thickness of from about 2 to 5 microns. Six of the coated screws were heated in a dry atmosphere of air to 300° C. for about forty minutes, and another six of the coated screws were autoclaved at about 130° C. to provide a basis for comparison. The twelve screws were implanted in rats as described above for fourteen days, after which the shear strength against removal was measured as described herein. Neither group of screws exhibited any measurable resistance to removal. Thus, when silver is the metal of an implant facing the bone, heating of the implant does not promote bone growth following implantation. Moreover, it was noted following removal that there was mild degeneration of the bone around the autoclaved screws, and massive degeneration of the bone around the heated screws.

It is of course appreciated that the rate of bone growth in the laboratory animals upon which the experiments reported herein were conducted is not the same as that of humans. In this respect, a period of two to three months might be required to achieve the degree of bone growth in a human which would correspond to that achieved in a period of two weeks with respect to the laboratory animals. With respect to the test results tabulated herein, however, such difference in growth rate is also applicable to the implantations of sterilized implants. Accordingly, implants heat treated in accordance with the present invention and implanted in humans would provide a degree and rate of bone growth far superior to that which is achieved without heat treatment.

While considerable emphasis has been placed on the studies made and the results thereof tabulated herein, it is to be distinctly understood that the foregoing descriptive matter is to be interpreted merely as illustrative of the present invention and not as a limitation.

Having thus described the invention, it is claimed:

1. A method of treating a metal prosthetic device prior to surgical implantation to enhance bone growth relative thereto following implantation comprising, providing a metal prosthetic device having an exposed surface devoid in its entirely of silver, and heating said device in a dry atmosphere to a temperature between about 180° C. and about 300° C.

2. The method according to claim 1, wherein said heating of said device is to a temperature of from about 280° C. to about 300° C.

3. The method according to claim 1, wherein said heating of said device at said temperature is for a period of at least twenty minutes.

4. The method according to claim 1, wherein said heating of said device at said temperature is for a period of from about twenty minutes to about three hours.

5. The method according to claim 1, wherein said atmosphere is air.

6. The method according to claim 1, wherein the metal of the prosthetic device is a metal or metal alloy selected from the group consisting of stainless steel, cobalt alloy and titanium alloy.

7. The method according to claim 6, wherein said heating is for a period of from about twenty minutes to about three hours.

8. The method according to claim 7, wherein said heating is to a temperature of from about 280° C. to about 300° C.

9. The method according to claim 1, wherein said heating of said device is to a temperature of from about 250° C. to about 300° C.

10. The method according to claim 1, wherein said heating of said device is to a temperature of from about 250° C. to about 300° C. for a period of at least twenty minutes.

11. The method according to claim 10, wherein said heating is to a temperature of from about 280° C. to about 300° C.

* * * * *